(12) United States Patent
Krusor et al.

(10) Patent No.: US 11,806,544 B2
(45) Date of Patent: Nov. 7, 2023

(54) MEDICAL DEVICE WITH MODIFIABLE VIEW OF AN ELECTROCARDIOGRAM

(71) Applicant: Stryker Corporation, Kalamazoo, MI (US)

(72) Inventors: Blaine Krusor, Seattle, WA (US); Fred W. Chapman, Newcastle, WA (US); Tyson G. Taylor, Bothell, WA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/558,436

(22) Filed: Dec. 21, 2021

(65) Prior Publication Data

US 2022/0193434 A1    Jun. 23, 2022

Related U.S. Application Data

(60) Provisional application No. 63/129,348, filed on Dec. 22, 2020.

(51) Int. Cl.

| G06F 3/0346 | (2013.01) |
| A61N 1/39 | (2006.01) |
| G06F 3/0488 | (2022.01) |
| G06F 3/0484 | (2022.01) |

(52) U.S. Cl.
CPC ......... *A61N 1/3993* (2013.01); *A61N 1/3904* (2017.08); *G06F 3/0346* (2013.01); *G06F 3/0484* (2013.01); *G06F 3/0488* (2013.01)

(58) Field of Classification Search
CPC .... G06F 3/0346; G06F 3/0484; G06F 3/0488; G06F 3/011; G06F 3/014; G06F 3/016; G06F 1/00; G06F 3/00; G06F 5/00; G06F 7/00; G06F 8/00; G06F 2207/00; G06F 2206/00; G06F 2205/00; G06F 2203/00; G06F 2201/00; G06F 2200/00; G06F 2115/00; G06F 2113/00; G06F 2111/00; G06F 2101/00; G06F 40/00
See application file for complete search history.

(56) References Cited

U.S. PATENT DOCUMENTS

| 2010/0235782 | A1* | 9/2010 | Powell | G16H 40/67 715/764 |
| 2019/0329053 | A1* | 10/2019 | Engman | A61N 1/3968 |
| 2020/0352462 | A1* | 11/2020 | Pedalty | A61B 5/346 |
| 2021/0128003 | A1* | 5/2021 | Brennan | A61B 5/4836 |
| 2022/0072321 | A1* | 3/2022 | O'Connor | G16H 40/67 |

* cited by examiner

*Primary Examiner* — Rayeez R Chowdhury
(74) *Attorney, Agent, or Firm* — Lee & Hayes, P.C.

(57) ABSTRACT

Various systems, methods, and devices related to modifying views of a multi-lead electrocardiogram (ECG), as well as identifying notations associated with the multi-lead ECG, are described. An example method includes displaying graphical elements in a first arrangement. The graphical elements respectively depict electrical signals indicative of an electrical activity of a heart. The example method further includes detecting a signal indicative of a display selection, and, based on the display selection, rearranging the graphical elements from the first arrangement to a second arrangement.

20 Claims, 5 Drawing Sheets

MEDICAL DEVICE WITH MODIFIABLE VIEW OF AN ELECTROCARDIOGRAM

CROSS-REFERENCE TO RELATED APPLICATION

This application claims the priority of U.S. Provisional Application No. 63/129,348, which was filed on Dec. 22, 2020 and is incorporated by reference herein in its entirety.

BACKGROUND

An electrocardiogram (ECG) is indicative of the electrical activity of a patient's heart. In various examples, an ECG is obtained via multiple ECG leads (e.g., twelve or fifteen ECG leads), which correspond to the electrical activity of the patient's heart detected from different angles. Rescuers and care providers utilize the ECG to diagnose a condition of the patient. For example, a pattern in the ECG can be indicative of an arrhythmia, such as ventricular fibrillation (VF), ST-elevation myocardial infarction (STEMI), or other serious conditions that require immediate medical treatment.

Traditionally, waveforms of the ECG leads are printed on paper. The waveforms are often printed in a standard nonanatomical sequence. In this nonanatomical sequence, the waveforms are presented in a sequence wherein the corresponding angles are non-consecutive. Alternatively, ECG leads can be presented in an anatomical sequence known as the "Cabrera" sequence. In the Cabrera sequence, the waveforms are presented in a sequence wherein the corresponding angles are consecutive. In cases where a rescuer prints the ECG waveforms associated with a patient at the scene of an emergency, the rescuer physically passes the printed ECG to other individuals, such as another care provider when the patient is being transported to a clinical environment.

DETAILED DESCRIPTION

Various problems associated with printed ECGs are addressed by the present disclosure. First, the printed ECG is static and cannot be switched between the standard and Cabrera sequences. Thus, if a first rescuer prints an ECG in a standard format and passes the printed ECG to a second rescuer with a preference for the Cabrera format, the second rescuer cannot view the printed ECG in the preferred Cabrera format without re-printing the ECG. In high-stress rescue environments in which important care decisions are dependent on diagnosis of the patient's ECG, this mismatch can prevent the second rescuer from efficiently or accurately diagnosing the patient, which can delay appropriate care for the patient. Second, the printed ECG provides a fixed snapshot of the patient's ECG, which can prevent the rescuers from identifying real-time changes in the ECG. Third, if the printed ECG becomes lost or damaged, any annotations or notes that the rescuer may have written on the printed ECG are inaccessible to the next care provider in the chain of care. These and other technological problems are addressed by implementations of the present disclosure.

Various implementations described herein relate to techniques for displaying graphical elements indicative of multiple leads of an ECG, simultaneously, on a screen of a medical device. In various cases, the medical device selects or modifies the arrangement of the graphical elements based on a user input signal. For instance, the medical device displays the graphical elements in a Cabrera or standard arrangement based on the user input signal. Thus, different users with different preferences can use the medical device to view the same ECG using their preferred formats. In particular examples, the graphical elements include waveforms that can be updated in real-time with the patient's ECG. Further, in some cases, the medical device can receive user input signals indicative of notations by a rescuer and associated with the ECG and store the notations with the ECG. Data indicative of the notations is transferred to other clinical devices, such that other clinical providers can review the ECG with the notations of the rescuer.

Various implementations will now be described with reference to the accompanying figures.

Figure 1:
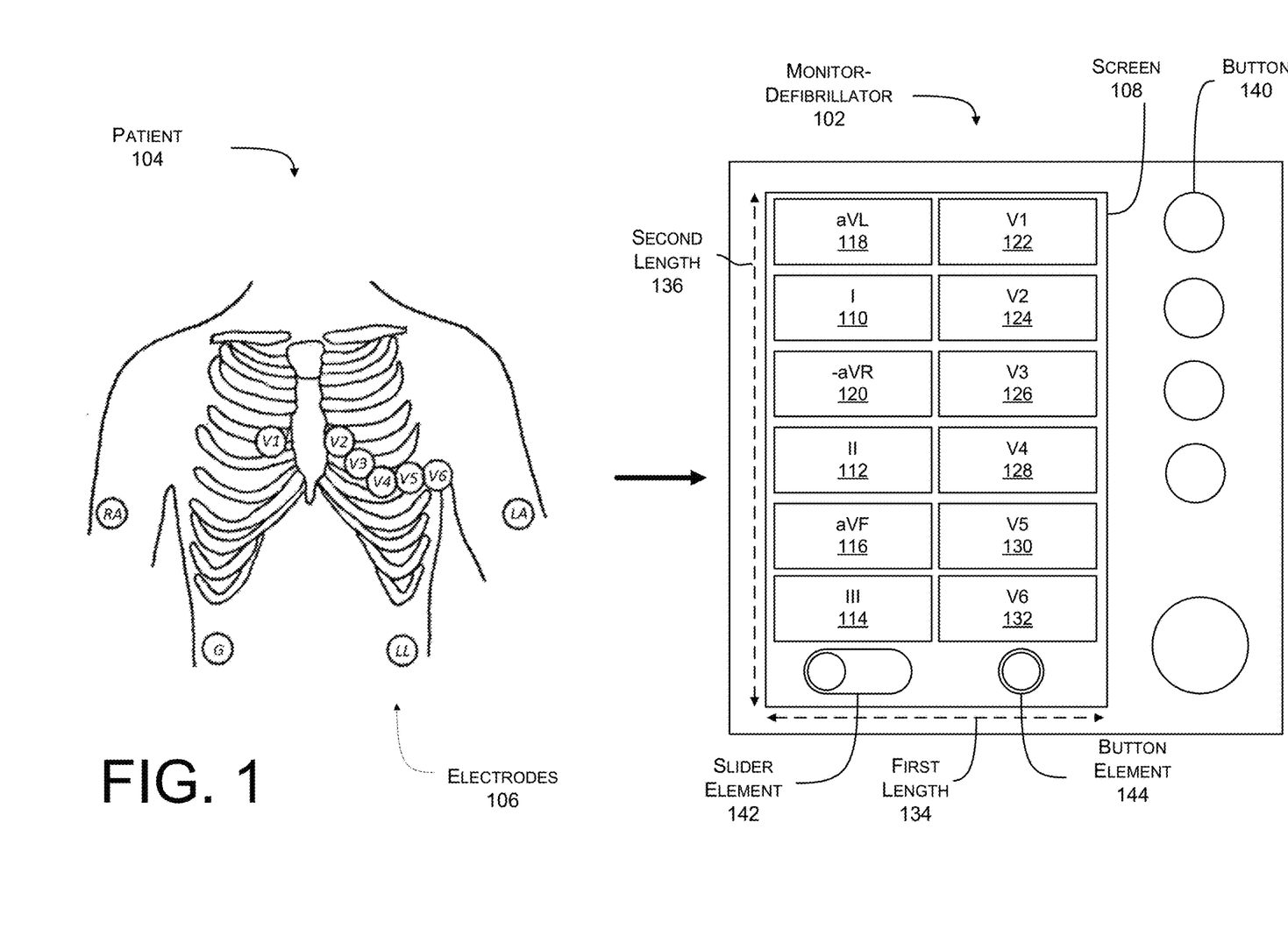
FIG. 1 illustrates an example environment including a monitor-defibrillator displaying a 12-lead ECG of a patient in a Cabrera format.

FIG. 1 illustrates an example environment 100 including a monitor-defibrillator 102 displaying a 12-lead ECG of a patient 104 in a Cabrera format. Ten ECG electrodes 106 are in contact with the patient 104. Four electrodes 106 correspond to the patient's limbs 104. For example, the electrodes 106 include a right arm (RA) electrode, a left arm (LA) electrode, a right leg (RL) or ground (G) electrode, and a left leg (LL) electrode. In addition, the electrodes 106 include precordial electrodes, including an electrode even with the fourth intercostal space (ICS) on the right margin of the patient's sternum 104 (V1), an electrode even with the fourth ICS on the left margin of the patient's sternum (V2), an electrode even with the fifth ICS along the patient's mid-clavicular line 104 (V4), an electrode placed between V2 and V4 (V3), an electrode even with the fifth ICS and an anterior axillary line of the patient 104 (V5), and an electrode even with the fifth ICS and a mid-axillary line of the patient 104 (V6).

The monitor-defibrillator 102 is configured to detect relative voltage differences between various electrode pairs 106. For example, although not illustrated in FIG. 1, the monitor-defibrillator 102 includes a detection circuit that is connected to the electrodes 106 by wired connections. In particular, the monitor-defibrillator 102 detects the relative voltages of various combinations of the electrodes. These relative voltages can be referred to as "leads." Graphical elements indicative of the leads are displayed on a monitor-defibrillator 102 screen 108.

Lead I 110 corresponds to the voltage of RA with respect to LA. Lead II 112 corresponds to the voltage of RA with respect to the voltage of LL. Lead III 114 corresponds to the voltage of LL with respect to the voltage of LA. Lead I 110, lead II 112, and lead III 114 can be referred to as "Einthoven leads" herein, which correspond to relative voltages between the vertices of Einthoven's triangle. RL or G may be used as the ground for the measurements of lead I 110, lead II 112, and lead III 114.

Other leads are unipolar leads representative of the voltage difference between a virtual electrode the other electrodes 106. The voltage of the virtual electrode, also known as Wilson's terminal ($V_W$), is defined according to the following Equation 1:

$$V_W = \frac{1}{3}(RA + LA + LL) \quad \text{Equation 1}$$

Lead aVF 116, lead aVL 118, and lead –aVR 120 are referred to as "augmented leads." Lead aVF 116 corresponds to the voltage of LL relative to $V_W$. Lead aVL 118 corresponds to the voltage of LA relative to $V_W$. Lead –aVR 120 corresponds to the voltage of $V_W$ relative to RA. The Einthoven leads and the augmented leads are collectively referred to as "limb leads."

Lead V1 122, lead V2 124, lead V3 126, lead V4 128, lead V5 130, and lead V6 132 are referred to as "precordial leads," and respectively correspond to the relative voltages between $V_W$ and the precordial electrodes. Lead V1 122 corresponds to the voltage of electrode V1 relative to $V_W$. Lead V2 124 corresponds to the voltage of electrode V2 relative to $V_W$. Lead V3 126 corresponds to the voltage of electrode V3 relative to $V_W$. Lead V4 128 corresponds to the voltage of electrode V4 relative to $V_W$. Lead V5 130 corresponds to the voltage of electrode V5 relative to $V_W$. Lead V6 132 corresponds to the voltage of electrode V6 relative to $V_W$.

Collectively, the twelve leads including lead I 110, lead II 112, lead III 114, lead aVF 116, lead aVL 118, lead –aVR 120, lead V1 122, lead V2 124, lead V3 126, lead V4 128, lead V5 130, and lead V6 132 are referred to as a "12-lead ECG." In some implementations, the monitor-defibrillator 102 detects a "15-lead ECG" that includes the twelve leads as well as three additional leads corresponding to the voltages of three posterior electrodes relative to $V_W$. The posterior electrodes include V7, V8, and V9. Electrode V7 is placed on a left posterior auxiliary line of the patient 104. V8 is placed on a tip of the left scapula of the patient 104. V9 is placed on a left paraspinal region of the patient 104. V7, V8, and V9 are all placed in the same horizontal plane as V6.

In the example illustrated in FIG. 1, the graphical elements corresponding to the leads 110 to 132 are displayed by the screen 108 in a first arrangement. The first arrangement, for instance, is a Cabrera arrangement wherein the graphical elements corresponding to the limb leads 110 to 120 are output in an anatomical order. In the Cabrera arrangement, the graphical elements corresponding to the leads 110 to 132 are displayed in the following order: lead aVL 118, lead I 110, lead –aVR 120, lead II 112, lead aVF 116, and lead III 118. In the first arrangement, the limb leads 110 to 120 are output in a first column and the precordial leads 122 to 132 are output in a second column. Each column includes six rows of graphical elements corresponding to limb leads. Thus, the screen 108 simultaneously displays the 12-lead ECG in the first arrangement.

The first arrangement corresponds to a portrait arrangement. For example, the screen 108 outputs the graphical elements corresponding to the leads 110 to 132 on a rectangular surface that includes a first length 134 and a second length 136. The first length 134 is shorter than the second length 138. Each of the graphical elements corresponding to the leads 110 to 132 includes a voltage waveform with respect to time, in various examples. That is, each waveform includes a time axis and a voltage axis, wherein the time axis is nonparallel to the voltage axis. In the portrait arrangement, the time axis of each of the waveforms is parallel to the first length 134 and the voltage axis of each of the waveforms is parallel to the second length 138.

In various implementations, a user selects the first arrangement of the graphical elements. The monitor-defibrillator 102 includes various input devices by which the user provides an input signal that indicates a selection of the first arrangement of the graphical elements. For example, the monitor-defibrillator 102 includes a button 140. In some cases, the button 140 is actuatable, such that the monitor-defibrillator 102 identifies the selection based on the button 140 being actuated by the user. In some cases, the button 140 includes a touch sensor configured to receive a signal indicative of the selection.

According to some cases, the screen 108 is a touchscreen that includes touch sensors. The monitor-defibrillator 102, for example, identifies the selection based on a signal detected by at least one of the touch sensors. In some cases, the monitor-defibrillator 102 identifies the selection based on a swipe signal detected by the touch sensors. The swipe signal is generated, for instance, by a user's finger touching and moving along the surface of the screen 108. In some examples, the monitor-defibrillator 102 identifies the selection based on a swirl signal detected by the touch sensors. The swirl signal is generated, for instance, by a user's finger touching and moving along the surface of the screen 108 in a curved path.

In some examples, the monitor-defibrillator 102 visually outputs a slider element 142 on the screen 108. The slider element 142 includes a shape that is moveable between a first position and a second position. The shape is illustrated in FIG. 1 as a circle in the first position. In some cases, the monitor-defibrillator 102 identifies the selection based on a signal received by at least one touch sensor overlapping the slider element 142. For example, the shape of the slider element is in the second position, a sensor overlapping the second position detects a swipe signal from the second position to the first position. The monitor-defibrillator 102 outputs the shape in the first position when the first arrangement is selected, for instance.

The monitor-defibrillator 102 outputs a button element 144 on the screen 108, in some cases. In various examples, the monitor-defibrillator 102 identifies the selection based on a signal received by at least one touch sensor overlapping the button element 144. In some cases, the monitor-defibrillator 104 outputs the button element 114 with a first color or shading when the first arrangement is selected.

According to various implementations, the monitor-defibrillator 102 identifies the selection based on a position, a movement, or an orientation of the monitor-defibrillator 102 that is detected by a position sensor within the monitor-defibrillator 102. For instance, the monitor-defibrillator 102 includes an accelerometer that is configured to detect a movement of the monitor-defibrillator 102. In some cases, the monitor-defibrillator 102 includes a gyroscope that is configured to detect an orientation of the monitor-defibrillator 102 relative to the direction of gravity. For example, the gyroscope may be configured to detect a relative angle between the first length 134 of the screen 108 and the direction of gravity or a relative angle between the second length 136 of the screen 108 and the direction of gravity. According to some implementations, the monitor-defibrillator 102 identifies the selection of the first arrangement when the orientation of the monitor-defibrillator 102 is in a first range. For instance, the monitor-defibrillator 102 identifies the selection of the first arrangement when the relative angle between the second length 136 and the direction of gravity is greater than a first angle (e.g., −90 degrees, −60 degrees, −45 degrees, etc.) and less than a second angle (e.g., 90 degrees, 60 degrees, 45 degrees, etc.).

In addition, the monitor-defibrillator 102 is configured to display the graphical elements corresponding to the leads 110 to 132 in a second arrangement that is different than the first arrangement. In various implementations, the user of the monitor-defibrillator 102 can cause the monitor-defibrillator 102 to switch between displaying the graphical elements in the first arrangement and the second arrangement. For instance, the monitor-defibrillator 102 rearranges the graphical elements between the first arrangement and the second arrangement based on detecting any of the input signals described herein.

Figure 2:
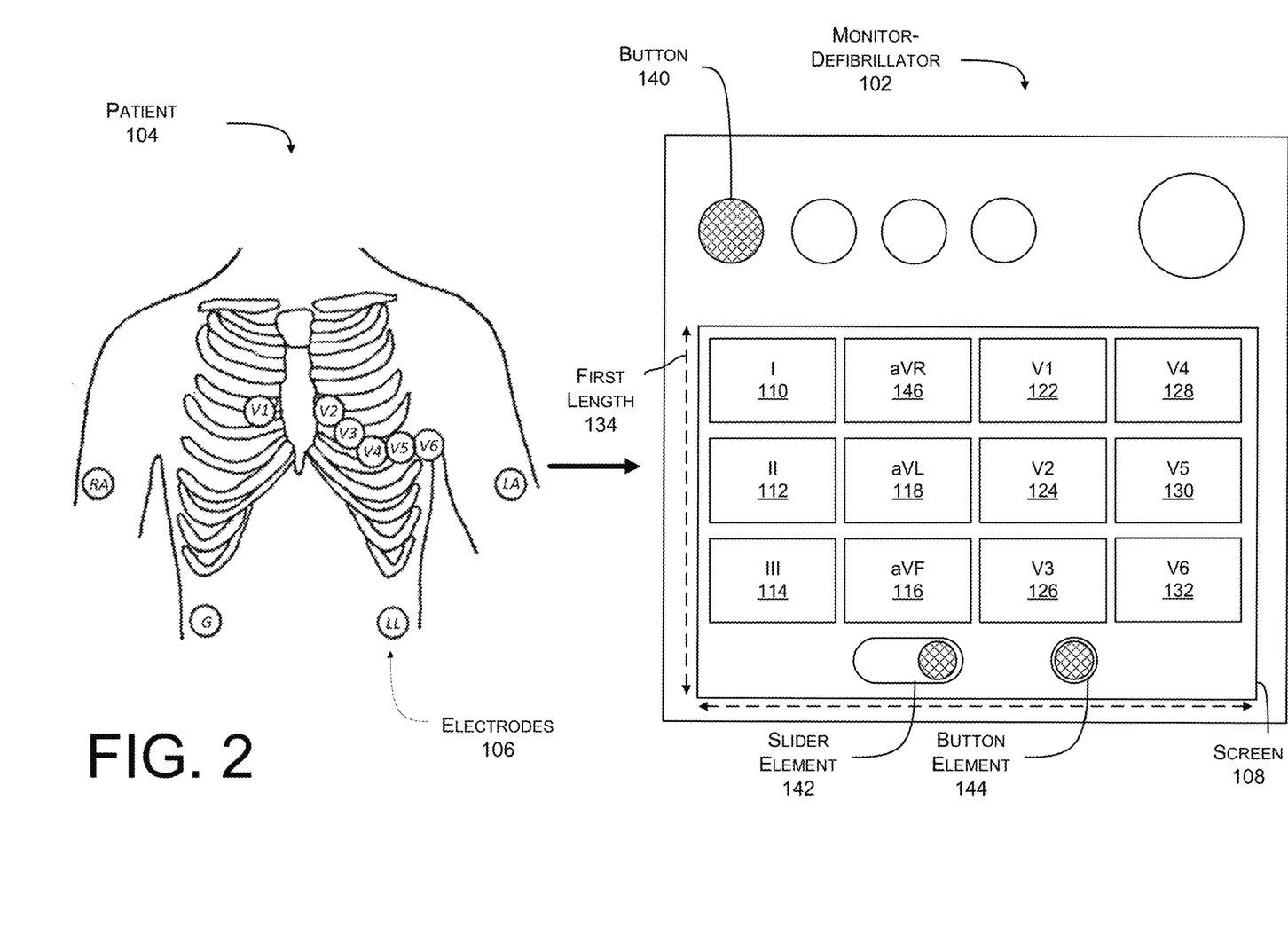
FIG. 2 illustrates an example environment including the monitor-defibrillator displaying a 12-lead ECG of the patient in a standard format.

FIG. 2 illustrates an example environment 200 including the monitor-defibrillator 102 displaying a 12-lead ECG of the patient 104 in a standard format. In FIG. 2, the monitor-defibrillator 102 displays similar graphical elements to those displayed by the monitor-defibrillator 102 in FIG. 1. However, the graphical element corresponding to the –aVR lead 120 is replaced with a graphical element corresponding to an aVR lead 146, which corresponds to the voltage of RA relative to $V_W$.

In the example illustrated in FIG. 2, the graphical elements are displayed by the screen 108 in the second arrangement, which is different than the first arrangement. The second arrangement, for instance, is a standard arrangement wherein the graphical elements corresponding to the limb leads 110 to 118 and 146 are output in a non-anatomical order. In the standard arrangement, the graphical elements corresponding to the limb leads 110 to 118 and 146 are displayed in the following order: lead I 110, lead II 112, lead III 114, lead aVR 146, lead aVL 118, and lead aVF 116. In the second arrangement, the graphical elements corresponding to the Einthoven leads (lead I 110, lead II 112, and lead III 114) are output in a first column, the graphical elements corresponding to the augmented leads (lead aVR 146, lead aVL 118, and lead aVF 116) are output in a second column, and the precordial leads 122 to 132 are output in third and fourth columns. Each column includes three rows of graphical elements corresponding to limb leads. Thus, the screen 108 simultaneously displays the 12-lead ECG in the second arrangement.

The second arrangement corresponds to a landscape arrangement. In the landscape arrangement, the time axis of each of the waveforms in the graphical elements is parallel to the second length 136 and the voltage axis of each of the waveforms is parallel to the first length 134.

In various implementations, a user selects the second arrangement of the graphical elements. At least one of the input devices of the monitor-defibrillator 102 detect an input signal indicating a selection of the second arrangement of the graphical elements. In some cases, the button 140 is actuatable, such that the monitor-defibrillator 102 identifies the selection based on the button 140 being actuated by the user. In some cases, the button 140 includes a touch sensor configured to receive a signal indicative of the selection.

According to some cases, the screen 108 is a touchscreen that includes touch sensors. The monitor-defibrillator 102, for example, identifies the selection based on a signal detected by at least one of the touch sensors. In some cases, the monitor-defibrillator 102 identifies the selection based on a swipe signal detected by the touch sensors. The swipe signal is generated, for instance, by a finger of the user touching and moving along the surface of the screen 108. In some examples, the monitor-defibrillator 102 identifies the selection based on a swirl signal detected by the touch sensors. The swirl signal is generated, for instance, by the finger of the user touching and moving along the surface of the screen 108 in a curved path.

In some examples, the monitor-defibrillator 102 identifies the selection using the slider element 142 or the button element 144. In some cases, the monitor-defibrillator 102 identifies the selection based on a signal received by at least one touch sensor overlapping the slider element 142. For example, the shape of the slider element is in the first position, a sensor overlapping the first position detects a swipe signal from the first position to the second position. The monitor-defibrillator 102 outputs the shape in the second position when the second arrangement is selected, for instance. In various examples, the monitor-defibrillator 102 identifies the selection based on a signal received by at least one touch sensor overlapping the button element 144. In some cases, the monitor-defibrillator 104 outputs the button element 114 with a second color or shading when the second arrangement is selected.

According to various implementations, the monitor-defibrillator 102 identifies the selection based on a position, a movement, or an orientation of the monitor-defibrillator 102 that is detected by the position sensor within the monitor-defibrillator 102. According to some implementations, the monitor-defibrillator 102 identifies the selection of the second arrangement when the orientation of the monitor-defibrillator 102 is in a second range. For instance, the monitor-defibrillator 102 identifies the selection of the second arrangement when the relative angle between the first length 134 and the direction of gravity is greater than a first angle (e.g., –90 degrees, –60 degrees, –45 degrees, etc.) and less than a second angle (e.g., 90 degrees, 60 degrees, 45 degrees, etc.).

In various examples, the graphical elements displayed in the first arrangement and the second arrangement represent a "paper-quality ECG." For example, each graphical element includes a grid and the grid includes boxes. As displayed on the screen 108, each box is 1 millimeter (mm) by 1 mm. In a direction parallel to the time axis, each box represents 0.02 seconds or 0.04 seconds. In a direction parallel to the voltage axis, each box represents 0.1 millivolts (mV). In various examples, the screen 108 is a high-definition screen or ultra-high-definition screen, such that each waveform, as displayed by the screen 108, is precisely depicted on the screen.

In some implementations, the graphical elements displayed in the first arrangement and the second arrangement are animated or otherwise updated in real-time as the ECG leads change over time. For instance, the electrodes 106 are in contact with the patient 104 and continuing to detect voltages indicative of the electrical activity of the patient's heart 104 in real-time. The graphical elements include waveforms that are updated, substantially in real-time, based on the voltages as they are detected by the electrodes 106.

Figure 3:
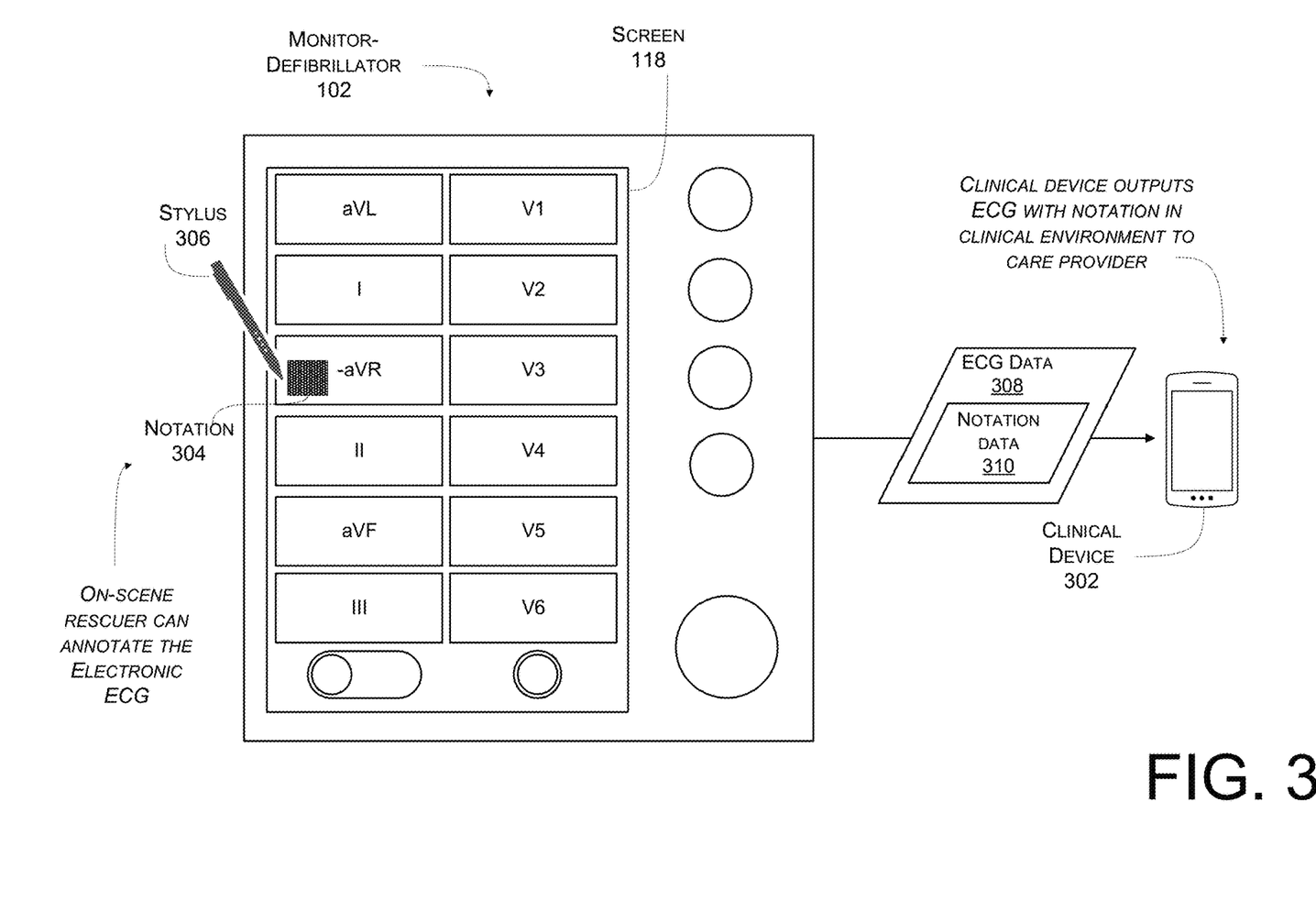
FIG. 3 illustrates an example environment of the monitor-defibrillator communicating with an external clinical device.

FIG. 3 illustrates an example environment 300 of the monitor-defibrillator 102 communicating with an external clinical device 302. In various examples of the present disclosure, the monitor-defibrillator 102 is portable and configured to communicate with the external clinical device 302 over a wired connection, a wireless connection, or both. In some cases, the monitor-defibrillator 102 is carried to the scene of a patient (e.g., the patient 104), who is experiencing cardiac arrest or some other medical ailment.

While at the scene, the monitor-defibrillator 102 is configured to monitor the patient. For instance, the monitor-defibrillator 102 detects a 12-lead ECG of the patient and outputs the 12-lead ECG in the form of various graphical elements on the screen 108. Because the monitor-defibrillator 102 is portable, the monitor-defibrillator 102 is configured to monitor the patient when the scene is outside of a clinical environment (e.g., a hospital). However, if the patient is transported to the clinical environment for further care, it is advantageous if care providers within the clinical environment are able to review the 12-lead ECG captured at the scene. Furthermore, some details regarding the patient's condition at the scene are relevant to the patient's care in the clinical environment and observable by the rescuer but are not captured in the ECG alone.

In various implementations, the user of the monitor-defibrillator 102 inputs a notation 304 into the monitor-defibrillator 102. In some examples, the notation 304 is associated with at least one of the graphical elements displayed on the monitor-defibrillator 102 screen 108. In some cases, the notation 304 indicates a condition of the patient. For example, the notation 304 indicates an observation by the rescuer about the patient at the scene (e.g., that the patient was alert, that the patient was unconscious, that the patient appeared to have a fever, that the patient was cool to the touch, etc.). In some examples, the notation 304 indicates an observation by the rescuer about how the ECG is being obtained (e.g., that lead LA was mistakenly reversed with lead RA on the patient, that lead aVR was obtained instead of lead –aVR, etc.).

The monitor-defibrillator 102, in some examples, detects the notation 304 using touch sensors integrated into the screen 108. The screen 108, for instance, is a touchscreen. In some cases, the touch sensors detect a pattern of movement of a stylus 306 touching the screen 108. The pattern corresponds to writing, such as letters, numbers, drawings, or the like. In some cases, the rescuer uses the stylus 306 to write words, letters, or numbers on the screen 108, which are detected by the touch sensors. In some examples, the monitor-defibrillator 102 performs pattern recognition to identify the words, letters, or numbers detected by the touch sensors. In some cases, the rescuer uses a different object, such as a finger, to input the pattern of movement detected by the touch sensors.

Optionally, the monitor-defibrillator 102 detects the notation 304 using a different type of input device. For example, the monitor-defibrillator 102 includes a microphone that detects the notation 304 as an audio signal spoken by the rescuer. In some examples, the monitor-defibrillator 102 performs speech recognition on the audio signal. In some examples, the monitor-defibrillator 102 includes a keyboard or other type of input device configured to detect the notation 304 as letters, words, or numbers input by the rescuer.

The monitor-defibrillator 102 generates ECG data 308 based on the ECG signal detected by the monitor-defibrillator 102. The ECG data 308 includes notation data 310 that is generated based on the notation 304. In some examples, the ECG data 308 is packaged in a common data format that is readable by the clinical device 302 without specialized software. For example, the ECG data 308 includes a text (.txt) file, a Portable Document Format (PDF or .pdf) file, a Joint Photographic Experts Group (JPEG or .jpeg) file, a Tagged Image File Format (TIFF or .tiff) file, a Graphics Interchange Format (GIF or .gif), a bitmap (BMP or .bmp) file, a Portable Network Graphics (PNG or .png) file, or the like.

In some implementations, the notation 304 and/or notation data 310 is stored in the form of a transparency or image layer. For example, the monitor-defibrillator 102, upon receiving an input signal from a user, may cause the notation 304 to appear as an overlay of the ECG on the screen 118 or may cause the notation 304 to disappear as the overlay. Accordingly, the user may input the notation 304 without concern of permanently obstructing the ECG.

In various examples, the ECG data 308 indicates various datapoints in the ECG lead signals. That is, the ECG data 308 includes data indicative of voltages and times of each of the ECG lead signals captured by the monitor-defibrillator 102. In some cases, the ECG data 308 includes images illustrating the waveforms of the ECG lead signals captured by the monitor-defibrillator 102.

The notation data 310 includes data indicative of the notation 304. For example, if the notation 304 includes a shape or pattern drawn on the screen 108, the notation data 310 includes an image of the notation 304. In some cases, the image of the notation 304 overlaps, or is adjacent to, the waveform of the ECG lead signal on which the shape or pattern was drawn. In some implementations, the notation data 310 includes text or binary data that is indicative of the notation 304. For instance, if the notation 304 includes an audio signal indicative of spoken words, or a shape or pattern that is in the shape of words, the monitor-defibrillator 102 performs speech and/or image recognition on the notation 304 in order to generate text or binary data indicating the words. The monitor-defibrillator 102, for example, uses a computing model to perform the speech recognition, such as at least one of a Hidden Markov model (HMM), a neural network (e.g., a time delay neural network (TDNN), a recurrent neural network (RNN), a convolutional neural network (CNN), etc.), and a connectionist temporal classification (CTC) model. In some cases, the monitor-defibrillator 102 uses a computing model to perform the pattern recognition, such as an optical character recognition (OCR) model or an intelligent word recognition model. In various examples, the text or binary data of the notation data 310 is associated, in the ECG data 308, with one or more of the ECG lead signals.

In various examples, the monitor-defibrillator 102 transmits the ECG data 308 to the clinical device 302 over a wireless connection. For instance, the monitor-defibrillator 102 transmits the ECG data 308 over a near field communication (NFC) connection, a BLUETOOTH® connection, a WIFI connection, a radio access network (RAN) connection, or an ultrasonic connection. According to some instances, the monitor-defibrillator 102 transmits the ECG data 308 over a wired connection, such as an electrical or optical connection. In some cases, the monitor-defibrillator 102 transmits the ECG data 308 in response to an input signal from the rescuer, which is detected by an input device of the monitor-defibrillator 102. For example, the monitor-defibrillator 102 transmits the ECG data 308 to the clinical device 302 when the rescuer transfers care of the patient to a care provider (e.g., a physician or nurse) associated with the clinical device 302.

Upon receiving the ECG data 308, the clinical device 302 is configured to output a graphical representation of the ECG data 308 to the care provider. In some cases, the clinical device 302 outputs an audio representation of the ECG data 308 to the care provider. Accordingly, the care provider is efficiently informed of the ECG of the patient as well as the notation 304 made by the rescuer at the scene.

Figure 4:
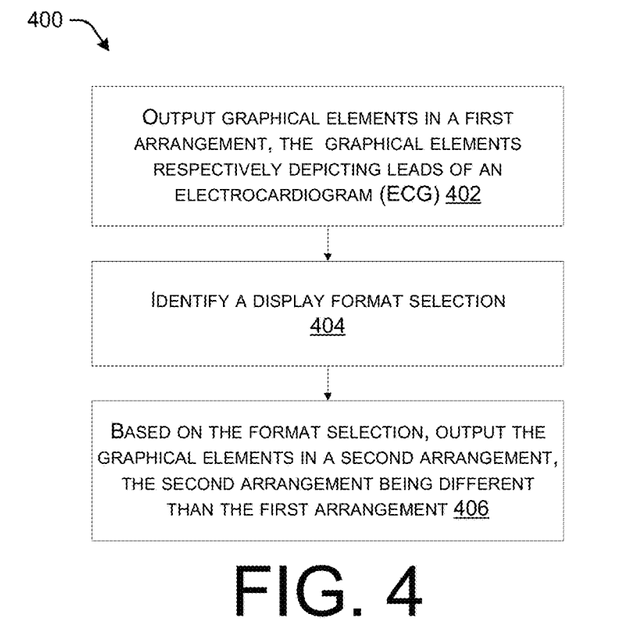
FIG. 4 illustrates an example process for modifying an arrangement of graphical elements corresponding to a multi-lead ECG.
Figure 5:
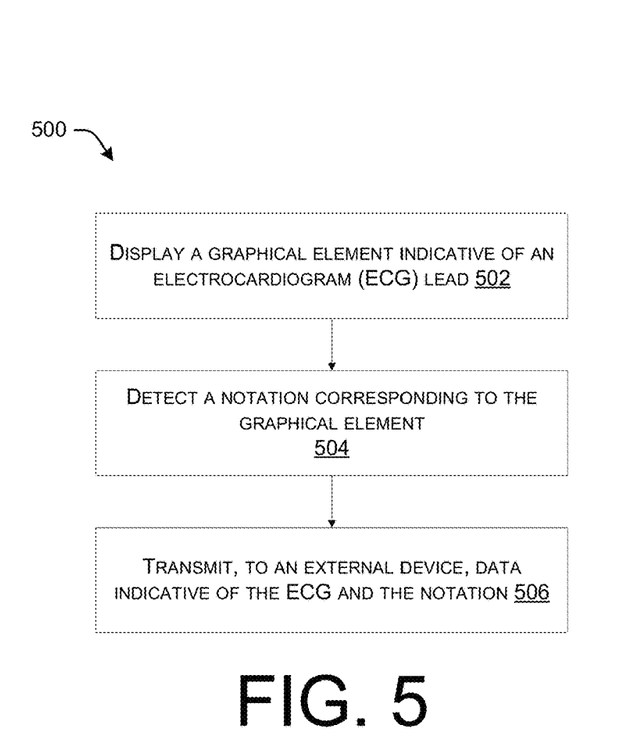
FIG. 5 illustrates an example process for providing a notation associated with an ECG to an external device.

FIGS. 4 and 5 illustrate example methods according to various implementations of the present disclosure. Although the methods illustrated in FIGS. 4 and 5 are illustrated in particular orders, implementations of the present disclosure are not so limited to the particular orders.

FIG. 4 illustrates an example process 400 for modifying an arrangement of graphical elements corresponding to a multi-lead ECG. The process 400 is performed by an entity, such as the monitor-defibrillator 102 described above with reference to FIGS. 1 to 3.

At 402, the entity outputs graphical elements in a first arrangement. The graphical elements respectively depict leads of an ECG. For example, the entity outputs twelve graphical elements corresponding to a 12-lead ECG, fifteen graphical elements corresponding to a 15-lead ECG, or the like. In various examples, the entity visually outputs the graphical elements on a screen. Each graphical element, for instance, depicts a waveform corresponding to a single lead of the ECG. The waveform includes a first axis corresponding to time and a second axis corresponding to voltage. In various implementations, the graphical elements are animated and depict the leads of the ECG in real-time as they are being detected. In some examples, the first arrangement is a Cabrera or a standard arrangement of the graphical elements. In various implementations, the screen is rectangular and the first arrangement is a portrait or a landscape arrangement. The graphical elements are displayed simultaneously on the screen in the first arrangement. For example, twelve graphical elements corresponding to the 12-lead ECG are displayed simultaneously on the screen in the first arrangement.

At 404, the entity identifies a display format selection. The display format selection is a selection of a second arrangement, in various examples. In some examples, an input device (e.g., a button or a touchscreen) of the entity identifies the display format selection by detecting an input signal. For example, the screen is a touchscreen and one or more touch sensors of the touchscreen detect a (e.g., swipe or a swirl) touch signal on a touchscreen surface. In some cases, the touch sensor(s) overlap a selectable graphical element output by the touchscreen, such as a button element or a slider element. In various examples, one or more position sensors of the entity identifies the display format selection. For example, an orientation sensor (e.g., an accelerometer or gyroscope) detects that the entity has been turned by a particular angle.

At 406, the entity outputs, based on the format selection, the graphical elements in the second arrangement. The second arrangement is different than the first arrangement. For example, the entity rearranges, rotates, and resizes the graphical elements that were output at 402. In particular instances, if the first arrangement was a Cabrera arrangement, the second arrangement is a standard arrangement, or vice versa. In some cases, if the first arrangement was a portrait arrangement, the second arrangement is a landscape arrangement, or vice versa. The graphical elements are displayed simultaneously on the screen in the second arrangement. For example, twelve graphical elements corresponding to the 12-lead ECG are displayed simultaneously on the screen in the second arrangement.

FIG. 5 illustrates an example process 500 for providing a notation associated with an ECG to an external device. The process 500 is performed by an entity, such as the monitor-defibrillator 102 described above with reference to FIGS. 1 to 3.

At 502, the entity displays a graphical element indicative of an ECG lead. For example, the entity outputs twelve graphical elements corresponding to a 12-lead ECG, fifteen graphical elements corresponding to a 15-lead ECG, or the like. In various examples, the entity visually outputs the graphical elements on a screen. Each graphical element, for instance, depicts a waveform corresponding to a single lead of the ECG. The waveform includes a first axis corresponding to time and a second axis corresponding to voltage. In various implementations, the graphical elements are animated and depict the leads of the ECG in real-time as they are being detected. The graphical elements are output in a first arrangement (e.g., a Cabrera arrangement) or a second arrangement (e.g., a standard arrangement).

At 504, the entity detects a notation corresponding to the graphical element. In some cases, the screen is a touchscreen and the entity detects the notation based on a pattern of a moving touch signal on the screen surface. For example, a user touches the screen surface with a stylus or finger and moves the stylus or finger in the pattern of the notation. In some examples, the entity includes a microphone that detects an audio signal corresponding to the notation. For instance, the user speaks words corresponding to the notation. The notation is drawn on the graphical element, for example. In some cases, the graphical element is selected simultaneously as the touchscreen detects the pattern or the microphone detects the audio signal.

At 506, the entity transmits, to the external device, data indicative of the ECG lead and the notation. For example, the data includes an image of the notation. In some cases, the entity uses pattern or speech recognition to convert the notation into a text or binary format. The data includes an image, text data, or binary data. In various examples, the data further indicates that the notation is associated with the ECG lead. In various implementations, the data is transmitted in a common data format. For example, the data includes a text file, a PDF file, a JPEG file, a TIFF file, a GIF file, a BMP file, a PNG file, or the like. The entity transmits the data over a wired connection, a wireless connection, or both, to the external device.

Figure 6:
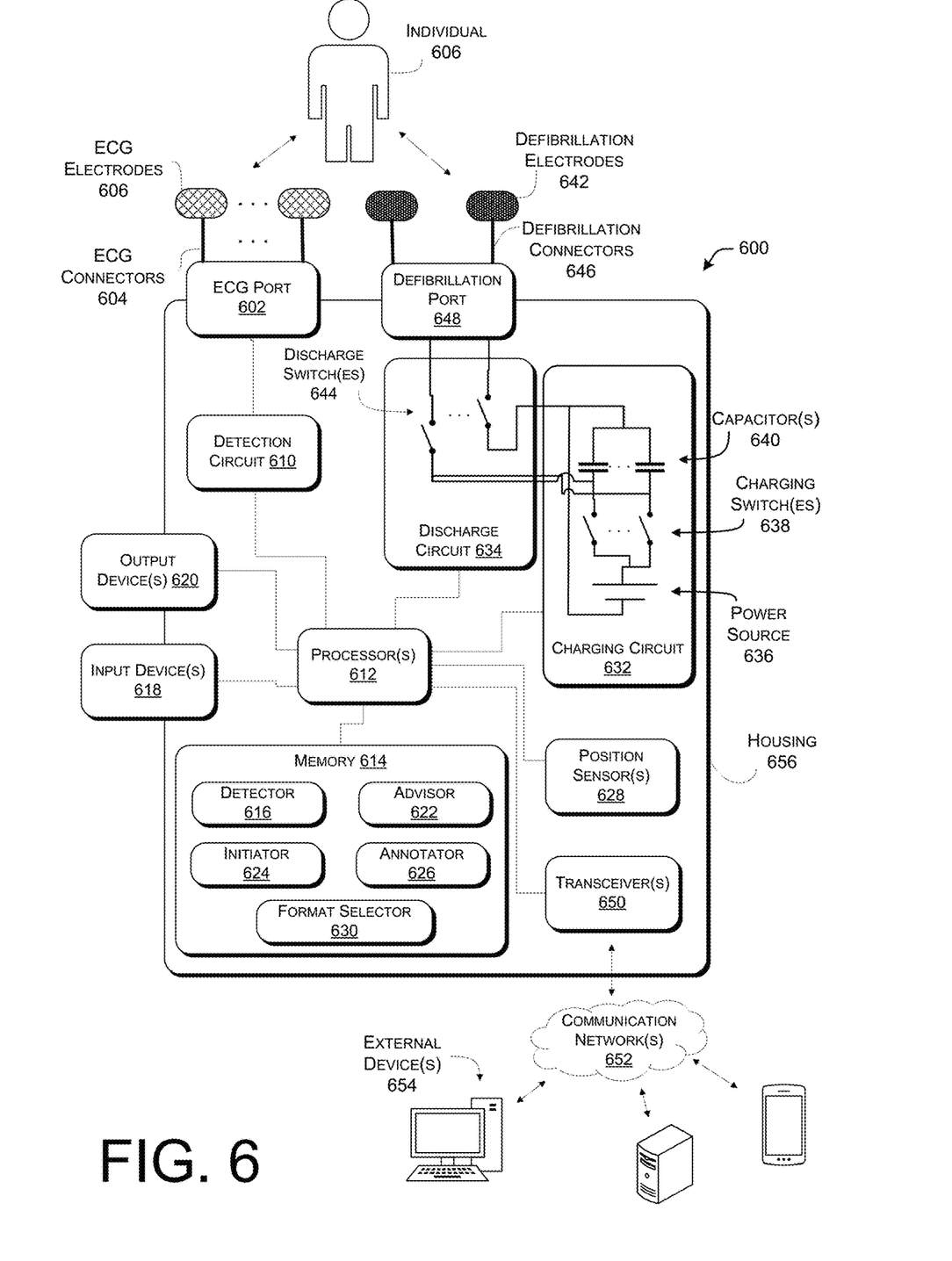
FIG. 6 illustrates an example of an external defibrillator configured to perform various functions described herein.

FIG. 6 illustrates an example of an external defibrillator 600 configured to perform various functions described herein. For example, the external defibrillator 600 is the monitor-defibrillator 102 described above with reference to FIGS. 1 to 3.

The external defibrillator 600 includes an ECG port 602 connected to multiple ECG connectors 604. In some cases, the ECG connectors 604 are removeable from the ECG port 602. For instance, the ECG connectors 604 are plugged into the ECG port 602. The ECG connectors 604 are connected to ECG electrodes 606, respectively. In various implementations, the ECG electrodes 606 are disposed on different locations on an individual 608. A detection circuit 610 is configured to detect relative voltages between the ECG electrodes 606. These voltages are indicative of the electrical activity of the individual's 608 heart.

In various implementations, the ECG electrodes 606 are in contact with the different locations on the individual's 608 skin. In some examples, a first one of the ECG electrodes 606 is placed on the skin between the heart and right arm of the individual 608, a second one of the ECG electrodes 606 is placed on the skin between the heart and left arm of the individual 608, and a third one of the ECG electrodes 606 is placed on the skin between the heart and a leg (either the left leg or the right leg) of the individual 608. In these examples, the detection circuit 608 is configured to measure the relative voltages between the first, second, and third ECG electrodes 606. Respective pairings of the ECG electrodes 606 are referred to as "leads," and the voltages between the pairs of ECG electrodes 606 are known as "lead voltages." In some examples, more than three ECG electrodes 606 are included, such that 5-lead or 12-lead ECG signals are detected by the detection circuit 610.

The detection circuit 610 includes at least one analog circuit, at least one digital circuit, or a combination thereof. The detection circuit 610 receives the analog electrical signals from the ECG electrodes 606, via the ECG port 602 and the ECG leads 604. In some cases, the detection circuit 610 includes one or more analog filters configured to filter noise and/or artifact from the electrical signals. The detection circuit 610 includes an analog-to-digital (ADC) in various examples. The detection circuit 610 generates a digital signal indicative of the analog electrical signals from the ECG electrodes 606. This digital signal can be referred to as an "ECG signal" or an "ECG."

In some cases, the detection circuit 610 further detects an electrical impedance between at least one pair of the ECG electrodes 606. For example, the detection circuit 610 includes, or otherwise controls, a power source that applies a known voltage across a pair of the ECG electrodes 606 and detects a resultant current between the pair of the ECG electrodes 606. The impedance is generated based on the applied voltage and the resultant current. In various cases, the impedance corresponds to respiration of the individual 608, chest compressions performed on the individual 608, and other physiological states of the individual 608. In various examples, the detection circuit 610 includes one or more analog filters configured to filter noise and/or artifact from the resultant current. The detection circuit 610 generates a digital signal indicative of the impedance using an ADC. This digital signal can be referred to as an "impedance signal" or an "impedance."

The detection circuit 610 provides the ECG signal and/or the impedance signal one or more processors 612 in the external defibrillator 600. In some implementations, the processor(s) 612 includes a central processing unit (CPU), a graphics processing unit (GPU), both CPU and GPU, or other processing unit or component known in the art.

The processor(s) 612 is operably connected to memory 614. In various implementations, the memory 612 is volatile (such as random-access memory (RAM)), non-volatile (such as read only memory (ROM), flash memory, etc.) or some combination of the two. The memory 614 stores instructions that, when executed by the processor(s) 612, causes the processor(s) 612 to perform various operations. In various examples, the memory 614 stores methods, threads, processes, applications, objects, modules, any other sort of executable instruction, or a combination thereof. In some cases, the memory 614 stores files, databases, or a combination thereof. In some examples, the memory 614 includes RAM, ROM, electrically erasable programmable read-only memory (EEPROM), flash memory, or any other memory technology. In some examples, the memory 614 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 612 and/or the external defibrillator 600. In some cases, the memory 614 at least temporarily stores the ECG signal and/or the impedance signal.

In various examples, the memory 614 includes a detector 616, which causes the processor(s) 612 to determine, based on the ECG signal and/or the impedance signal, whether the individual 608 is exhibiting a particular heart rhythm. For instance, the processor(s) 612 determines whether the individual 608 is experiencing a shockable rhythm that is treatable by defibrillation. Examples of shockable rhythms include ventricular fibrillation (VF) and pulseless ventricular tachycardia (V-Tach). In some examples, the processor(s) 612 determines whether any of a variety of different rhythms (e.g., asystole, sinus rhythm, atrial fibrillation (AF), etc.) are present in the ECG signal.

The processor(s) 612 is operably connected to one or more input devices 618 and one or more output devices 620. Collectively, the input device(s) 618 and the output device(s) 620 function as an interface between a user and the defibrillator 600. The input device(s) 618 is configured to receive an input from a user and includes at least one of a keypad, a cursor control, a touch-sensitive display, a voice input device (e.g., a speaker), a haptic feedback device, or any combination thereof. The output device(s) 620 includes at least one of a display, a speaker, a haptic output device, a printer, or any combination thereof. In various examples, the processor(s) 612 causes a display among the input device(s) 618 to visually output a waveform of the ECG signal and/or the impedance signal. In some implementations, the input device(s) 618 includes one or more touch sensors, the output device(s) 620 includes a display screen, and the touch sensor(s) are integrated with the display screen. Thus, in some cases, the external defibrillator 600 includes a touchscreen configured to receive user input signal(s) and visually output physiological parameters, such as the ECG signal and/or the impedance signal.

In some examples, the memory 614 includes an advisor 622, which, when executed by the processor(s) 612, causes the processor(s) 612 to generate advice and/or control the output device(s) 620 to output the advice to a user (e.g., a rescuer). In some examples, the processor(s) 612 provides, or causes the output device(s) 620 to provide, an instruction to perform CPR on the individual 608. In some cases, the processor(s) 612 evaluates, based on the ECG signal, the impedance signal, or other physiological parameters, CPR being performed on the individual 608 and causes the output device(s) 620 to provide feedback about the CPR in the instruction. According to some examples, the processor(s) 612, upon identifying that a shockable rhythm is present in the ECG signal, causes the output device(s) 620 to output an instruction and/or recommendation to administer a defibrillation shock to the individual 608.

The memory 614 also includes an initiator 624 which, when executed by the processor(s) 612, causes the processor(s) 612 to control other elements of the external defibrillator 600 in order to administer a defibrillation shock to the individual 608. In some examples, the processor(s) 612 executing the initiator 624 selectively causes the administration of the defibrillation shock based on determining that the individual 608 is exhibiting the shockable rhythm and/or based on an input from a user (received, e.g., by the input device(s) 618. In some cases, the processor(s) 612 causes the defibrillation shock to be output at a particular time, which is determined by the processor(s) 612 based on the ECG signal and/or the impedance signal.

In various cases, the memory 614 includes an annotator 626 which, when executed by the processor(s) 612, causes the processor(s) 612 to generate ECG data based on the ECG signal and to generate annotation data associated with the ECG data based on an input signal received by the input device(s) 616. For example, a touchscreen of the input device(s) 618 receives a signal indicative of a note associated with a lead of the ECG signal and the processor(s) 612 generate the annotation data based on the note. In some cases, the annotator 626 causes the processor(s) 612 to generate the annotation data by performing handwriting recognition or natural language processing based on the signal indicative of the note. In some cases, a microphone of the input device(s) 618 receives a signal indicative of the note and the processor(s) 612 generate the annotation data based on the note. For example, the annotator 626 causes the processor(s) 612 to generate the annotation data by performing speech recognition on the signal indicative of the note.

In some examples, the annotations or notes are stored as a transparency or image layer. When displayed, the annotations or notes are visually overlaid on the ECG, in various cases. According to some implementations, the annotator 626 causes the image layer including the annotations or notes to appear or disappear over the ECG on an output device (e.g., a screen).

According to various examples, the processor(s) 612 are operably connected to one or more position sensors 628. The position sensor(s) 628 are configured to identify a position, movement, or orientation of the external defibrillator 600. For example, the position sensor(s) 628 include a location service circuit (e.g., a Global Navigation Satellite System (GNSS) circuit, such as a Global Positioning System (GPS) circuit) configured to identify the position of the external defibrillator 600, an accelerometer configured to identify an acceleration of the external defibrillator 600, or a gyroscope configured to identify the orientation of the external defibrillator 600.

The memory 614 further includes a format selector 630, in various examples. When executed by the processor(s) 612, the format selector 630 causes the processor(s) 612 to identify a selected arrangement of graphical elements indicating the ECG leads of the ECG signal and to cause a screen of the output device(s) 620 to output the graphical elements in the selected arrangement. In some examples, the selected arrangement is a first arrangement (e.g., a Cabrera arrangement) or a second arrangement (e.g., a standard arrangement) of the ECG leads. According to various examples, the screen is rectangular, the first arrangement is a portrait arrangement, and the second arrangement is a landscape arrangement. The format selector 630, when executed by the processor(s) 612, causes the processor(s) 612 to identify the selected arrangement based on a format selection. In some cases, the processor(s) 612 identify the format selection based on a touchscreen of the input device(s) 618 receiving an input signal associated with a selectable GUI element (e.g., a touch input signal associated with a button or slider element output by the touchscreen), based on a button of the input device(s) 618 receiving an input signal, or based on a microphone of the input device(s) 618 receiving an auditory input signal. In some implementations, the processor(s) 612 identify the format selection based on a position, movement, or orientation of the external defibrillator 600 that is detected by the position sensor(s) 628. For instance, the processor(s) 612 determines that the first arrangement is the selected arrangement if the gyroscope of the position sensor(s) 628 detects that the screen of the external defibrillator 600 is oriented in a first orientation and determines that the second arrangement is the selected arrangement if the gyroscope of the position sensor(s) 628 detects that the screen of the external defibrillator 600 is oriented in a second orientation. In some cases, the processor(s) 612 determines that the selected arrangement switches between one arrangement and the other arrangement when the position sensor(s) 628 determines that the screen of the external defibrillator has been physically rotated greater than a threshold angle (e.g., an angle that is greater than 0 degrees and less than or equal to 90 degrees).

The format selector 630, in some implementations, causes the screen to output multiple graphical elements simultaneously. For instance, twelve graphical elements, respectively corresponding to twelve ECG leads, are output on the screen simultaneously. In some cases, fifteen graphical elements, respectively corresponding to fifteen ECG leads, are output on the screen simultaneously. For example, one of the arrangements may include the graphical elements in six rows and two columns, and another one of the arrangements may include the graphical elements in three rows and four columns.

The processor(s) 612 is operably connected to a charging circuit 632 and a discharge circuit 634. In various implementations, the charging circuit 632 includes a power source 636, one or more charging switches 638, and one or more capacitors 640. The power source 636 includes, for instance, a battery. The processor(s) 612 initiates a defibrillation shock by causing the power source 636 to charge at least one capacitor among the capacitor(s) 640. For example, the processor(s) 612 activates at least one of the charging switch(es) 638 in the charging circuit 632 to complete a first circuit connecting the power source 636 and the capacitor to be charged. Then, the processor(s) 612 causes the discharge circuit 634 to discharge energy stored in the charged capacitor across a pair of defibrillation electrodes 640, which are in contact with the individual 608. For example, the processor(s) 612 deactivates the charging switch(es) 638 completing the first circuit between the capacitor(s) 640 and the power source 636, and activates one or more discharge switches 644 completing a second circuit connecting the charged capacitor 640 and at least a portion of the individual 608 disposed between defibrillation electrodes 642.

The energy is discharged from the defibrillation electrodes 642 in the form of a defibrillation shock. For example, the defibrillation electrodes 642 are connected to the skin of the individual 608 and located at positions on different sides of the heart of the individual 608, such that the defibrillation shock is applied across the heart of the individual 608. The defibrillation shock, in various examples, depolarizes a significant number of heart cells in a short amount of time. The defibrillation shock, for example, interrupts the propagation of the shockable rhythm (e.g., VF or pulseless V-Tach) through the heart. In some examples, the defibrillation shock is 200 J or greater with a duration of 0.015 seconds. In some cases, the defibrillation shock has a multiphasic (e.g., biphasic) waveform. The discharge switch(es) 644 are controlled by the processor(s) 612, for example. In various implementations, the defibrillation electrodes 642 are connected to defibrillation connectors 646. The defibrillation connectors 646 are connected to a defibrillation port 648, in implementations. According to various examples, the defibrillation connectors 646 are removable from the defibrillation port 648. For example, the defibrillation connectors 646 are plugged into the defibrillation port 648.

In various implementations, the processor(s) 612 is operably connected to one or more transceivers 650 that transmit and/or receive data over one or more communication networks 652. For example, the transceiver(s) 650 includes a network interface card (NIC), a network adapter, a local area network (LAN) adapter, or a physical, virtual, or logical address to connect to the various external devices and/or systems. In various examples, the transceiver(s) 650 includes any sort of wireless transceivers capable of engaging in wireless communication (e.g., radio frequency (RF) communication). For example, the communication network(s) 652 includes one or more wireless networks that include a $3^{rd}$ Generation Partnership Project (3GPP) network, such as a Long Term Evolution (LTE) radio access network (RAN) (e.g., over one or more LE bands), a New Radio (NR) RAN (e.g., over one or more NR bands), or a combination thereof. In some cases, the transceiver(s) 650 includes other wireless modems, such as a modem for engaging in WI-FI®, WIGIG®, WIMAX®, BLUETOOTH®, or infrared communication over the communication network(s) 652.

The defibrillator 600 is configured to transmit and/or receive data (e.g., ECG data, notation data, impedance data, data indicative of one or more detected heart rhythms of the individual 608, data indicative of one or more defibrillation shocks administered to the individual 608, etc.) with one or more external devices 654 via the communication network(s) 652. The external devices 654 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 652. In some examples, the external device(s) 654 is located remotely from the defibrillator 600, such as at a remote clinical environment (e.g., a hospital). According to various implementations, the processor(s) 612 causes the transceiver(s) 650 to transmit data to the external device(s) 654. In some cases, the transceiver(s) 650 receives data from the external device(s) 654 and the transceiver(s) 650 provide the received data to the processor(s) 612 for further analysis.

In various implementations, the external defibrillator 600 also includes a housing 656 that at least partially encloses other elements of the external defibrillator 600. For example, the housing 656 encloses the detection circuit 610, the processor(s) 612, the memory 614, the charging circuit 632, the transceiver(s) 650, or any combination thereof. In some cases, the input device(s) 618 and output device(s) 620 extend from an interior space at least partially surrounded by the housing 656 through a wall of the housing 656. In various examples, the housing 656 acts as a barrier to moisture, electrical interference, and/or dust, thereby protecting various components in the external defibrillator 600 from damage.

In some implementations, the external defibrillator 600 is an automated external defibrillator (AED) operated by an untrained user (e.g., a bystander, layperson, etc.) and can be operated in an automatic mode. In automatic mode, the processor(s) 612 automatically identifies a rhythm in the ECG signal, makes a decision whether to administer a defibrillation shock, charges the capacitor(s) 640, discharges the capacitor(s) 640, or any combination thereof. In some cases, the processor(s) 612 controls the output device(s) 620 to output (e.g., display) a simplified user interface to the untrained user. For example, the processor(s) 612 refrains from causing the output device(s) 620 to display a waveform of the ECG signal and/or the impedance signal to the untrained user, in order to simplify operation of the external defibrillator 600.

In some examples, the external defibrillator 600 is a monitor-defibrillator utilized by a trained user (e.g., a clinician, an emergency responder, etc.) and can be operated in a manual mode or the automatic mode. When the external defibrillator 600 operates in manual mode, the processor(s) 612 cause the output device(s) 620 to display a variety of information that may be relevant to the trained user, such as waveforms indicating the ECG data and/or impedance data, notifications about detected heart rhythms, and the like.

EXAMPLE CLAUSES

1. An external defibrillator including: a detection circuit configured to detect electrical signals indicative of an electrical activity of the heart of an individual; a display screen configured to display a graphical user interface (GUI) including graphical elements corresponding to the electrical signals; an input device configured to detect a selection signal indicative of a display format selection; a processor; and memory storing instructions that, when executed by the processor, cause the processor to perform operations including: causing the display screen to display, based on the display format selection, the graphical elements in predetermined positions within the GUI.

2. The external defibrillator according to clause 1, wherein the input device includes a gyroscope, an accelerometer, a button, a touch sensor, or a microphone configured to detect the selection signal.

3. The external defibrillator according to clause 2, wherein the gyroscope or accelerometer is configured to detect the selection signal as a physical rotation of the input device, the button is configured to detect the selection signal as a physical touch, the touch sensor is configured to detect a touch moving against a surface of the display screen, or the microphone is configured to detect a sound.

4. The external defibrillator according to clause 3, wherein the physical rotation of the input device is greater than 0 degrees and less than or equal to 90 degrees.

5. The external defibrillator according to clause 3 or 4, the graphical elements being first graphical elements, the touch sensor being a first touch sensor, wherein the button includes an actuatable mechanism or a second touch sensor overlapping a second graphical element displayed on the display screen.

6. The external defibrillator according to any one of clauses 1 to 5, wherein causing the display screen to display, based on the display format selection, the graphical elements in the predetermined positions within the GUI includes causing the display screen to display a first group of the graphical elements in a first row, to display a second group of the graphical elements in a second row, and to display a third group of the graphical elements in a third row disposed between the first row and the second row.

7. The external defibrillator according to any one of clauses 1 to 6, wherein causing the display screen to display, based on the display format selection, the graphical elements in the predetermined positions within the GUI includes causing the display screen to display a first group of the graphical elements in a first column and to display a second group of the graphical elements in a second column.

8. The external defibrillator according to any one of clauses 1 to 7, wherein the graphical elements include twelve waveforms respectively corresponding to twelve leads of an electrocardiogram (ECG), the electrical signals including the twelve leads.

9. The external defibrillator according to any one of clauses 1 to 8, wherein the predetermined positions include a standard electrocardiogram (ECG) format or a Cabrera ECG format.

10. The external defibrillator according to clause 8 or 9, wherein the predetermined positions include a nonanatomical orientation of the twelve waveforms or an anatomical orientation of the twelve waveforms.

11. A medical device including: a display screen configured to: display a graphical user interface (GUI); a processor; and memory storing instructions that, when executed by the processor, cause the processor to perform operations including: determining a selected arrangement to display graphical elements depicting electrical signals indicative of an electrical activity of a heart; and causing the display screen to display the graphical elements in the selected arrangement within the GUI.

12. The medical device according to clause 11, wherein the display screen includes a touch sensor configured to detect a touch, and wherein determining the selected arrangement is based on the touch.

13. The medical device according to clause 11 or 12, wherein the medical device is an external defibrillator.

14. The medical device according to any one of clauses 11 to 13, further including: a transceiver configured to receive, from an external defibrillator, a signal indicative of the electrical signals.

15. The medical device according to any one of clauses 11 to 14, further including: an input device configured to receive an input signal, wherein determining the selected arrangement is based on the input signal.

16. The medical device according to any one of clauses 11 to 15, wherein the operations further include: causing the display screen to display the graphical elements in a default arrangement, the default arrangement being different than the selected arrangement, wherein causing the display screen to display the graphical elements in the selected arrangement includes causing the display screen to rearrange the graphical elements from the default arrangement to the selected arrangement.

17. The medical device according to any one of clauses 11 to 16, further including: a rotation sensor including a gyroscope or an accelerometer, the rotation sensor being configured to detect a rotation of the medical device, wherein determining the selected arrangement is based on the rotation of the medical device.

18. The medical device according to clause 17, wherein the rotation is greater than 0 degrees and less than or equal to 90 degrees.

19. The medical device according to clause 17 or 18, wherein the rotation includes: a first motion of the medical device in a first rotational direction, and a second motion of the medical device in a second rotational direction that is different than the first rotational direction.

20. A method for displaying an electronic electrocardiogram (ECG), the method including: displaying graphical elements in a first arrangement, the graphical elements respectively depicting electrical signals indicative of an electrical activity a heart; detecting a signal indicative of a display selection; and based on the display selection, rearranging the graphical elements from the first arrangement to the second arrangement.

21. The method according to clause 20, further including: detecting, by electrodes of an external defibrillator, the electrical signals, wherein displaying the graphical elements in the first arrangement includes displaying the graphical elements in the first arrangement by a display screen of the external defibrillator, and wherein rearranging the graphical elements from the first arrangement to the second arrangement includes displaying the graphical elements in the second arrangement by the display screen of the external defibrillator.

22. The method according to clause 20 or 21, further including: receiving, from an external defibrillator, data indicative of the electrical signals, wherein displaying the graphical elements in the first arrangement includes displaying the graphical elements in the first arrangement by a display screen of a computing device that is remote from the external defibrillator, and wherein rearranging the graphical elements from the first arrangement to the second arrangement includes displaying the graphical elements in the second arrangement by the display screen of the computing device.

23. The method according to any one of clauses 20 to 22, the signal being a first signal, the method further including: receiving a second signal indicative of a lock selection; and locking the graphical elements in the second arrangement.

24. The method according to any one of clauses 20 to 23, wherein detecting a signal indicative of a display selection includes detecting a rotation of a medical device.

25. The method according to any one of clauses 20 to 24, wherein the graphical elements include twelve waveforms respectively depicting twelve leads of the ECG, the electrical signals respectively corresponding to the twelve leads.

26. The method according to clause 25, wherein the first arrangement includes a standard ECG arrangement and the second arrangement includes a Cabrera ECG arrangement.

27. The method according to clause 25 or 26, wherein the first arrangement includes a Cabrera ECG arrangement and the second arrangement includes a standard ECG arrangement.

28. The method according to any one of clauses 20 to 27, the signal being a first signal, the method further including: detecting a second signal; and in response to detecting the second signal, enlarging a subset of the graphical elements.

29. The method according to clause 28, the subset being a first subset, the method further including: detecting a third signal; and in response to detecting the third signal, displaying an enlarged form of a second subset of the graphical elements, the second subset being different than the first subset.

30. The method according to any one of clauses 20 to 29, wherein detecting a signal indicative of a display selection includes receiving the signal from an external device.

31. The method according to any one of clauses 20 to 30, the graphical elements being first graphical elements, the method further including: detecting a digital notation corresponding to a particular graphical element among the first graphical elements; and displaying a second graphical element indicative of the digital notation within a distance of the particular graphical element.

32. An external defibrillator having a modifiable view of an electronic electrocardiogram (ECG), the external defibrillator including: a detection circuit configured to detect electrical signals indicative of an electrical activity of a heart; a display screen configured to display a graphical user interface (GUI); an input device configured to detect a signal indicative of a display format selection; a processor; and memory storing instructions that, when executed by the processor, cause the processor to perform operations including: causing the display screen to display, based on the display format selection and within the GUI, graphical elements in a particular arrangement, the graphical elements depicting the electrical signals, the particular arrangement including a standard ECG arrangement or a Cabrera ECG arrangement.

33. The external defibrillator according to clause 32, the signal being a first signal, the graphical elements being first graphical elements, wherein the input device is further configured to detect a second signal indicative of a notation, and wherein the operations further include: causing the display to display, within the GUI, a second graphical element depicting the notation.

34. The external defibrillator according to clause 33, wherein the second signal is an audible signal or a touch signal.

35. The external defibrillator according to clause 33 or 34, wherein the memory is further configured to store data indicative of the electrical signals and the notation.

36. The external defibrillator according to any one of clauses 33 to 35, wherein the data is stored as an image file or a Portable Document Format (PDF) file.

37. The external defibrillator according to any one of clauses 33 to 36, further including: a transceiver configured to transmit, to a clinical device, a third signal including the data.

38. The external defibrillator according to any one of clauses 33 to 37, further including: a transceiver configured to transmit, to an electronic medical record (EMR) server, a third signal including the data.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. An external defibrillator comprising:
   a detection circuit configured to detect, by electrodes, 12 or 15 electrocardiogram (ECG) signals indicative of an electrical activity of a heart of an individual;
   a display screen configured to display 12 or 15 graphical elements respectively corresponding to the 12 or 15 ECG signals, wherein a first graphical element represents a first electrical potential between a first combination of the electrodes during a time interval, and a second graphical element represents a second electrical potential between a second combination of the electrodes during the time interval;
   a user interface (UI) configured to selectively switch between a first arrangement and a second arrangement;
   a processor; and
   memory storing instructions that, when executed by the processor, cause the processor to perform operations comprising:
      in response to the UI selecting the first arrangement, displaying, via the display screen, a first row and a first column of third graphical elements in a portrait format, wherein the third graphical elements are positioned side by side one another in the first row, and the third graphical elements are positioned above or below one another in the first column; or
      in response to the UI selecting the second arrangement, displaying, via the display screen, a second row and a second column of fourth graphical elements in a landscape format, wherein the fourth graphical elements are positioned side by side one another in the second row, and the fourth graphical elements are positioned above or below one another in the second column.

2. The external defibrillator according to claim 1, further comprising:
   a gyroscope, an accelerometer, a button, a touch sensor, or a microphone configured to detect a selection signal indicative of a selection of the first arrangement or the second arrangement.

3. The external defibrillator according to claim 2, wherein the gyroscope or accelerometer is configured to detect the selection signal as a physical rotation of the gyroscope,
   the button is configured to detect the selection signal as a physical touch,
   the touch sensor is configured to detect a touch moving against a surface of the display screen, or
   the microphone is configured to detect a sound.

4. The external defibrillator according to claim 3, wherein the physical rotation of the gyroscope is greater than 0 degrees and less than or equal to 90 degrees.

5. The external defibrillator according to claim 3, the touch sensor being a first touch sensor, wherein the button comprises an actuatable mechanism or a second touch sensor overlapping a fifth graphical element displayed on the display screen.

6. The external defibrillator according to claim 1,
   wherein displaying the first row and the first column of the third graphical elements further comprises displaying, via the display screen and in response to the UI selecting the first arrangement, a first group of the 12 or 15 graphical elements in the first row, a second group of the 12 or 15 graphical elements in a third row, and a third group of the 12 or 15 graphical elements in a fourth row disposed between the first row and the third row.

7. The external defibrillator according to claim 1,
   wherein displaying the first row and the first column of the third graphical elements further comprises displaying, via the display screen and in response to the UI selecting the first arrangement, a first group of the 12 or 15 graphical elements in the first column and to display a second group of the 12 or 15 graphical elements in a third column.

8. The external defibrillator according to claim 1, wherein the 12 or 15 graphical elements comprise 12 or 15 waveforms respectively corresponding to the 12 or 15 ECG signals.

9. The external defibrillator according to claim 1, wherein the portrait format corresponds to a standard ECG format, and the landscape format corresponds to a Cabrera ECG format.

10. The external defibrillator according to claim 8, wherein the portrait format comprises an anatomical orientation of the 12 or 15 graphical elements, and the landscape format comprises a non-anatomical orientation of the 12 or 15 graphical elements.

11. The external defibrillator according to claim 1, wherein the UI is further configured to receive a selection signal indicative of the first arrangement or the second arrangement, the first arrangement is utilized to present 12 or 15 waveforms of the 12 or 15 ECG signals in a first sequence, and the second arrangement is utilized to present the 12 or 15 waveforms of the 12 or 15 ECG signals in a second sequence that is different from the first sequence.

12. A medical device comprising:
   a detection circuit configured to detect, by electrodes, 12 or 15 electrocardiogram (ECG) signals indicative of an electrical activity of a heart of an individual;
   a display screen configured to display 12 or 15 graphical elements respectively corresponding to the 12 or 15 ECG signals, wherein a first graphical element represents a first electrical potential between a first combination of the electrodes during a time interval, and a second graphical element represents a second electrical potential between a second combination of the electrodes during the time interval;
   a user interface (UI) configured to selectively switch between a first arrangement and a second arrangement, wherein the first arrangement is utilized to present 12 or 15 waveforms of the 12 or 15 ECG signals in a first sequence, and the second arrangement is utilized to present the 12 or 15 waveforms of the 12 or 15 ECG signals in a second sequence that is different from the first sequence;
   a processor; and
   memory storing instructions that, when executed by the processor, cause the processor to perform operations comprising:
      in response to the UI selecting the first arrangement, displaying, via the display screen, a first row and a first column of third graphical elements in a portrait format, wherein the third graphical elements are positioned side by side one another in the first row, and the third graphical elements are positioned above or below one another in the first column; or
      in response to the UI selecting the second arrangement, displaying, via the display screen, a second row and a second column of fourth graphical elements in a landscape format, wherein the fourth graphical elements are positioned side by side one another in the second row, and the fourth graphical elements are positioned above or below one another in the second column.

13. The medical device according to claim 12, wherein the display screen comprises a touch sensor configured to detect a touch, and
wherein selectively switching between the first arrangement and the second arrangement is in response to the touch.

14. The medical device according to claim 12, wherein the medical device comprises an external defibrillator.

15. The medical device according to claim 12, further comprising:
a transceiver configured to receive, from an external defibrillator, a signal in response to electrical signals indicative of an electrical activity of a heart of an individual.

16. The medical device according to claim 12, wherein the operations further comprise:
displaying, via the display screen, the 12 or 15 graphical elements in a default arrangement, the default arrangement being different than a selected arrangement, the selected arrangement indicating the first arrangement or the second arrangement, and
wherein displaying, via the display screen, the 12 or 15 graphical elements in the selected arrangement comprises rearranging, via the display screen, the 12 or 15 graphical elements from the default arrangement to the selected arrangement.

17. The medical device according to claim 12, further comprising:
a rotation sensor comprising a gyroscope or an accelerometer, the rotation sensor being configured to detect a rotation of the medical device,
wherein selectively switching between the first arrangement and the second arrangement is in response to the rotation of the medical device.

18. The medical device according to claim 17, wherein the rotation is greater than 0 degrees and less than or equal to 90 degrees.

19. The medical device according to claim 17, wherein the rotation comprises:
a first motion of the medical device in a first rotational direction, and
a second motion of the medical device in a second rotational direction that is different than the first rotational direction.

20. The medical device according to claim 12, wherein the UI is further configured to receive a selection signal indicative of the first arrangement or the second arrangement, the portrait format comprises an anatomical orientation of the 12 or 15 graphical elements, and the landscape format comprises a non-anatomical orientation of the 12 or 15 graphical elements.

* * * * *